United States Patent
Matsukuma

(10) Patent No.: US 9,157,854 B2
(45) Date of Patent: Oct. 13, 2015

(54) SCATTERED LIGHT-TYPE SMOKE DETECTION APPARATUS

(75) Inventor: Hidenari Matsukuma, Tokyo (JP)

(73) Assignee: HOCHIKI CORPORATION, Tokyo (JP)

( * ) Notice: Subject to any disclaimer, the term of this patent is extended or adjusted under 35 U.S.C. 154(b) by 20 days.

(21) Appl. No.: 14/128,421

(22) PCT Filed: May 29, 2012

(86) PCT No.: PCT/JP2012/063791
§ 371 (c)(1),
(2), (4) Date: Dec. 20, 2013

(87) PCT Pub. No.: WO2013/001966
PCT Pub. Date: Jan. 3, 2013

(65) Prior Publication Data
US 2014/0111803 A1     Apr. 24, 2014

(30) Foreign Application Priority Data
Jun. 30, 2011   (JP) ................... 2011-146724

(51) Int. Cl.
*G01N 21/53* (2006.01)
*G08B 17/107* (2006.01)

(52) U.S. Cl.
CPC ............. *G01N 21/53* (2013.01); *G08B 17/107* (2013.01); *G01N 2201/0642* (2013.01)

(58) Field of Classification Search
USPC .......... 356/336–339, 436–438; 250/216, 573, 250/574, 578.1; 340/630, 628, 619
See application file for complete search history.

(56) References Cited

U.S. PATENT DOCUMENTS

| | | | |
|---|---|---|---|
| 4,596,465 A | * | 6/1986 | Nagashima .................... 356/338 |
| 4,678,921 A | * | 7/1987 | Nakamura et al. ............ 250/574 |

(Continued)

FOREIGN PATENT DOCUMENTS

| | | |
|---|---|---|
| JP | U3-44794 A | 4/1991 |
| JP | 4-81997 A | 3/1992 |

(Continued)

OTHER PUBLICATIONS

International Search Report for International Application No. PCT/JP2012/063791 mailed Aug. 28, 2012. 10 pages.

(Continued)

*Primary Examiner* — Sang Nguyen
(74) *Attorney, Agent, or Firm* — Brian J. Colandreo; Jeffrey T. Placker; Holland & Knight LLP

(57) ABSTRACT

To provide a scattered light-type smoke detection apparatus in which internally scattered light in a smoke detection space can be suppressed to improve the S/N ratio. A scattered light-type smoke detection apparatus includes: a smoke detection space that is provided in a light-shielded area that is light-shielded from the outside, into which smoke particles flow from the outside; a light emitter for emitting detection light toward the smoke detection space; and a light receiver for receiving scattered light caused by detection light emitted by the light emitter and scattered by smoke particles flowing into the smoke detection space, wherein the scattered light-type smoke detection apparatus includes an internally scattered light suppressing means for transmitting and guiding part or the whole of detection light emitted by the light emitter and passing through the smoke detection space to a predetermined area or the outside of the light-shielded area to suppress internally scattered light within the light-shielded area.

3 Claims, 9 Drawing Sheets

(56) References Cited

U.S. PATENT DOCUMENTS

| | | | | |
|---|---|---|---|---|
| 4,758,733 | A | * | 7/1988 | Mochizuki ............... 250/574 |
| 5,021,677 | A | * | 6/1991 | Igarashi et al. ........... 250/574 |
| 5,400,014 | A | * | 3/1995 | Behlke et al. ............ 340/630 |
| 5,430,307 | A | * | 7/1995 | Nagashima ............... 250/574 |
| 5,587,790 | A | * | 12/1996 | Nagashima ............... 356/338 |
| 5,670,947 | A | * | 9/1997 | Nagashima ............... 340/628 |
| 5,929,988 | A | * | 7/1999 | Ichikawa ................. 356/338 |
| 6,914,535 | B2 | * | 7/2005 | Matsukuma et al. ........ 340/630 |
| 7,746,239 | B2 | * | 6/2010 | Nagashima ............... 340/630 |
| 2005/0242967 | A1 | * | 11/2005 | Yamasaki et al. ......... 340/630 |
| 2008/0018485 | A1 | * | 1/2008 | Kadwell et al. ........... 340/630 |
| 2011/0068936 | A1 | * | 3/2011 | Shimada et al. ........... 340/584 |

FOREIGN PATENT DOCUMENTS

| | | |
|---|---|---|
| JP | 6-342497 A | 12/1994 |
| JP | 7-182584 A | 7/1995 |
| JP | 8-261930 A | 10/1996 |
| JP | 9-198584 A | 7/1997 |
| JP | 2000-65740 A | 3/2000 |
| JP | 2000-65741 A | 3/2000 |
| JP | 2005-309735 A | 4/2005 |

OTHER PUBLICATIONS

Written Opinion for International Application No. PCT/JP2012/063791 mailed Aug. 28, 2012. 6 pages.

International Preliminary Report on Patentability issued on Jan. 7, 2014 in PCT/JP2012/063791.

Patent Examination Report No. 1 issued on Nov. 6, 2014 in the counterpart Australian Application numbered 2012277058.

* cited by examiner (a)

(b)

SCATTERED LIGHT-TYPE SMOKE DETECTION APPARATUS

RELATED APPLICATIONS

The subject application is a U.S. National Stage Application of International Application No. PCT/JP2012/063791, filed on 29 May 2012, which claims the priority of Japanese Patent Application No.: 2011-146724, filed on 30 Jun. 2011, the contents of which are herein incorporated by reference in its entirety.

TECHNICAL FIELD

The present invention relates to a scattered light-type smoke detection apparatus.

BACKGROUND ART

Conventionally, a scattered light-type smoke detection apparatus is used that detects smoke utilizing a light scattering phenomenon caused by smoke. The scattered light-type smoke detection apparatus includes: a smoke detection space into which smoke flows from the outside; a light-shielding structure for blocking light from the outside from entering the smoke detection space while allowing smoke from the outside to flow into the smoke detection space; a light emitter for emitting detection light toward the smoke detection space; and a light receiver for receiving detection light scattered by smoke flowing into the smoke detection space (referred to as scattered light) and converting the received scattered light to electric signal.

In such a scattered light-type smoke detection apparatus, as a member, including the light-shielding structure, for forming the smoke detection space, for example, a material such as a black resin for absorbing detection light from the light emitter is used, but it cannot significantly reduce reflection from the surface of the member. Due to this, conventionally, light emitted by the light emitter and passing through the smoke detection space may, for example, be reflected by a flat surface part, an end face, an edge part or the like of a light-shielding member included in the light-shielding structure, the reflected light (referred to as internally scattered light) entering the light receiver. In this case, the steady level of the detection output of the light receiver (referred to as zero point level) may be elevated to decrease the S/N ratio, thereby reducing reliability.

Thus, a scattered light-type smoke detection apparatus that is designed to reduce internally scattered light has also been proposed. For example, a scattered light-type smoke sensor has been proposed in which a light-shielding member is ingeniously shaped and arranged such that detection light from a light emitter is reflected by the surface of the light-shielding member, as much of the reflected detection light as possible being discharged to the outside of a smoke detection space (for example, see Patent Document 1). [Prior Art Document] [Patent Document]

[Patent Document 1] Japanese Patent Application Laid-Open No. H6-342497

SUMMARY OF THE INVENTION

Problems to be Solved by the Invention

It is an object of the present invention to solve the problems of the above mentioned prior arts.

Means for Solving the Problems

One aspect of the present invention provides a scattered light-type smoke detection apparatus according to claim 1 includes: a smoke detection space that is provided in a light-shielded area that is light-shielded from the outside, into which smoke particles flow from the outside; a light emitter for emitting detection light toward the smoke detection space; and a light receiver for receiving scattered light caused by detection light emitted by the light emitter and scattered by smoke particles flowing into the smoke detection space, wherein the scattered light-type smoke detection apparatus includes an internally scattered light suppressing means for transmitting and guiding part or the whole of detection light emitted by the light emitter and passing through the smoke detection space to a predetermined area or the outside of the light-shielded area to suppress internally scattered light within the light-shielded area.

BRIEF DESCRIPTION OF THE DRAWINGS

FIG. 1 A diagram illustrating a smoke sensor to which a scattered light-type smoke detection apparatus in accordance with a first embodiment is applied, in which FIG. 1(a) is a front view showing an appearance of the smoke sensor, and FIG. 1(b) is a side view schematically showing the internal structure of the smoke sensor shown in FIG. 1(a).

MODE FOR CARRYING OUT THE INVENTION

Embodiments of a scattered light-type smoke detection apparatus in accordance with the invention are described below in detail with reference to the accompanying drawings. First, "[I] Basic concept of embodiments" is described. Then, "[II] Specific details of embodiments" is described. Finally, "[III] Variation of embodiments" is described. However, it should be noted that the invention is not limited to the embodiments.

[I] Basic Concept of Embodiments

First, a basic concept common to the embodiments is described. The scattered light-type smoke detection apparatus in accordance with the embodiments includes: a smoke detection space that is a space provided in a light-shielded area that is light-shielded from the outside, into which smoke particles flow from the outside; a light emitter for emitting detection light toward the smoke detection space; and a light receiver for receiving scattered light caused by detection light scattered by smoke particles flowing into the smoke detection space, the apparatus detecting smoke based on the light receiving signal output from the light receiver.

The scattered light-type smoke detection apparatus in accordance with the embodiments can be applied to any appropriate purpose, for example, can be applied to a smoke-type residential fire alarm installed in a kitchen, staircase, bedroom, living room or the like of a residence, and a smoke sensor of an automatic fire alarm facility.

One feature of the scattered light-type smoke detection apparatus in accordance with the embodiments is that, generally, it has an internally scattered light suppressing means for suppressing internally scattered light within the light-shielded area by causing detection light emitted by the light emitter and passing through the smoke detection space to enter a translucent light-guiding means and then transmitting and guiding the detection light to a predetermined area or the outside of the light-shielded area.

This can further suppress internally scattered light caused by detection light passing through the smoke detection space and reflected by a light-shielding member, than before, and can improve the S/N ratio by appropriately adjusting internally scattered light.

[II] Specific Details of Embodiments

Next, specific details of the embodiments in accordance with the invention are described. Note that, in the embodiments below, the scattered light-type smoke detection apparatus applied to a smoke sensor is described as an example.

[First Embodiment]

First, a first embodiment is described. In the first embodiment, detection light emitted by a light emitter and passing through a smoke detection space is collected by a lens and caused to enter a light-attenuating structure provided in a predetermined area, which guides the entering light to the light-attenuating structure to be attenuated.

(Configuration)

Figure 1:
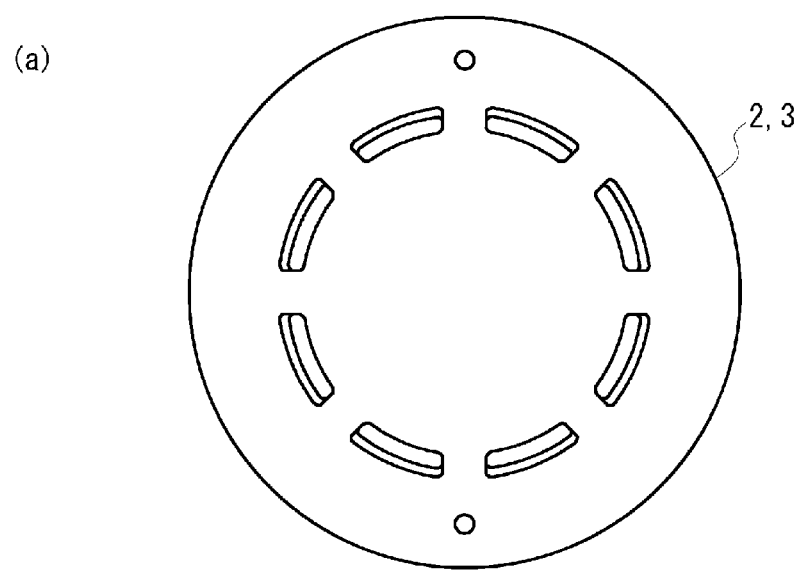
Figure 1:
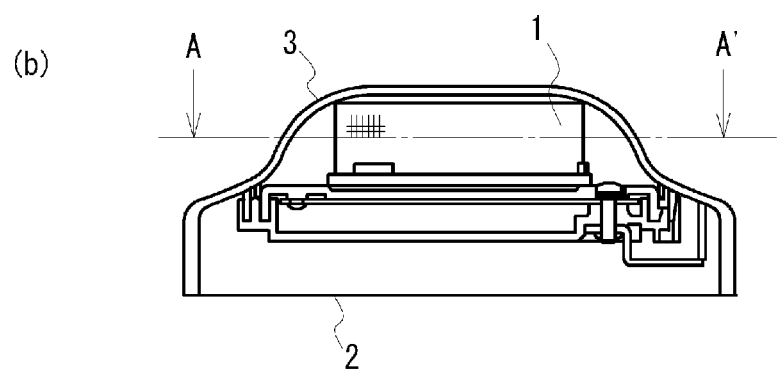

First, the configuration of a scattered light-type smoke detection apparatus in accordance with the first embodiment is described. FIG. 1 illustrates a smoke sensor to which the scattered light-type smoke detection apparatus in accordance with the first embodiment is applied. FIG. 1(*a*) is a front view showing an appearance of the smoke sensor. FIG. 1(*b*) is a side view schematically showing in a see-through mode an internal structure of the smoke sensor shown in FIG. 1(*a*). As shown in FIG. 1, a scattered light-type smoke detection apparatus 1 is contained in a chassis 3 of a smoke sensor 2.

Figure 2:
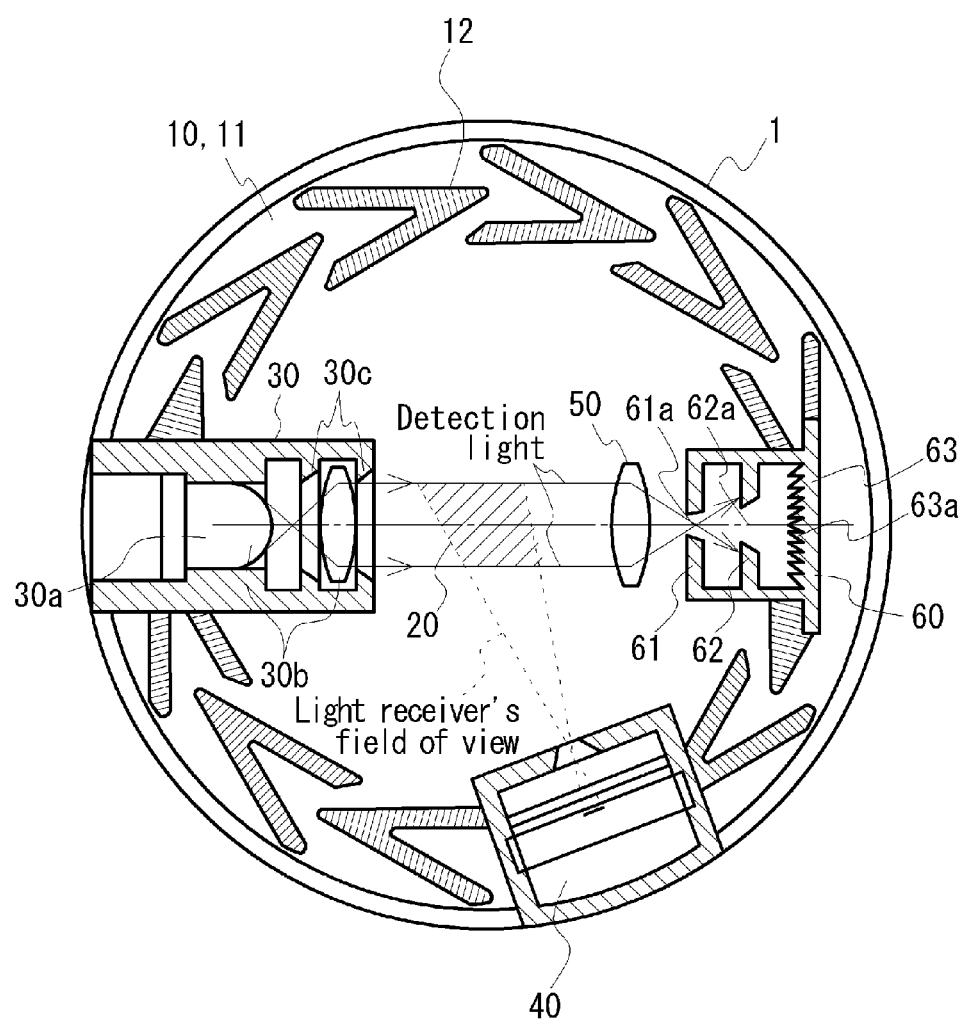
FIG. 2 A cross-sectional view showing a cross section taken along the line A-A' of the scattered light-type smoke detection apparatus shown in FIG. 1(b).

FIG. 2 is a cross-sectional view showing a cross section taken along the line A-A' of the scattered light-type smoke detection apparatus 1 shown in FIG. 1(*b*). As shown in FIG. 2, the scattered light-type smoke detection apparatus 1 includes a main body 10, a smoke detection space 20, a light emitter 30, a light receiver 40, a lens 50 and a light-attenuating structure 60, and further includes a circuit board (not shown) including a given electric circuit.

(Configuration—Main Body)

Here, the main body 10 includes a base plate (bottom plate) 11, light-shielding members 12 and a cover plate (top plate) not shown. The base plate 11 and the cover plate are placed in generally parallel to each other. The light-shielding members 12 are placed between the base plate 11 and the cover plate. An area enclosed by a light-shielding structure including the base plate 11, the light-shielding members 12 and the cover plate is a light-shielded area that is light-shielded from the outside. For example, as shown in FIG. 2, the light-shielding members 12 including a curved part are arranged so as to prevent external light from entering the inside of the light-shielded area from the outside directly or via a low-order reflection (e.g., a primary or secondary reflection), which forms an inflow path along which smoke particles flow into the light-shielded area from the outside while forming part of the light-shielding structure for light-shielding the light-shielded area from the outside of the light-shielded area. Note that the light-shielding members 12 are fixed to the base plate 11 or the cover plate.

(Configuration—Smoke Detection Space)

The smoke detection space 20 is a space provided in the light-shielded area that is light-shielded from the outside, into which smoke particles flow from the outside and in which scattered light causing effective smoke detection signal may occur. The smoke particles pass through a space between the light-shielding members 12 and flow into the smoke detection space 20 from the outside of the light-shielded area.

(Configuration—Light Emitter)

The light emitter 30 intermittently emits and radiates detection light toward the smoke detection space 20. The light emitter 30 is placed in the light-shielded area such that the light axis of the light emitter 30 crosses the effective field of view light axis of the light receiver 40 in proximity to the center of the light-shielded area. Here, the light axis of the light emitter 30 refers to a light flux center axis along which detection light propagates. For example, the light emitter 30 uses an LED (light-emitting diode) 30*a* as a light source and concentrates detection light emitted by the LED 30*a* to a predetermined light flux using a lens 30*b* and aperture 30*c* to radiate the light flux toward the smoke detection space 20.

(Configuration—Light Receiver)

The light receiver 40 receives scattered light generated by detection light radiated by the light emitter 30 and scattered by smoke particles flowing into the smoke detection space 20, in synchronization with emission of light by the light emitter 30, and outputs electric signal (smoke detection signal) depending on the amount of light of the received scattered light. The light receiver 40 is placed in the light-shielded area such that the light-receiving axis of the light receiver 40 crosses the light axis of the light emitter 30 in proximity to the center of the light-shielded area. The proximity of the crossing of the light axes corresponds to the smoke detection space 20. For example, a photodiode may be used for the light receiver 40.

(Configuration—Lens)

As shown in FIG. 2, the lens 50 collects detection light radiated by the light emitter 30 and passing through the smoke detection space 20, and radiates the collected light to a predetermined area (in FIG. 2, an area in which the light-attenuating structure 60 is provided). This causes detection light radiated by the light emitter 30 and passing through the smoke detection space 20 to be transmitted and guided to the predetermined area. The lens 50 is placed between the smoke detection space 20 and the light-shielding members 12 such that the light axis of the lens 50 corresponds with the light axis of the light emitter 30. Note that the lens 50 may also be configured to collect detection light not passing through the smoke detection space 20 (detection light propagating outside the smoke detection space).

(Configuration—Light-Attenuating Structure)

Figure 3:
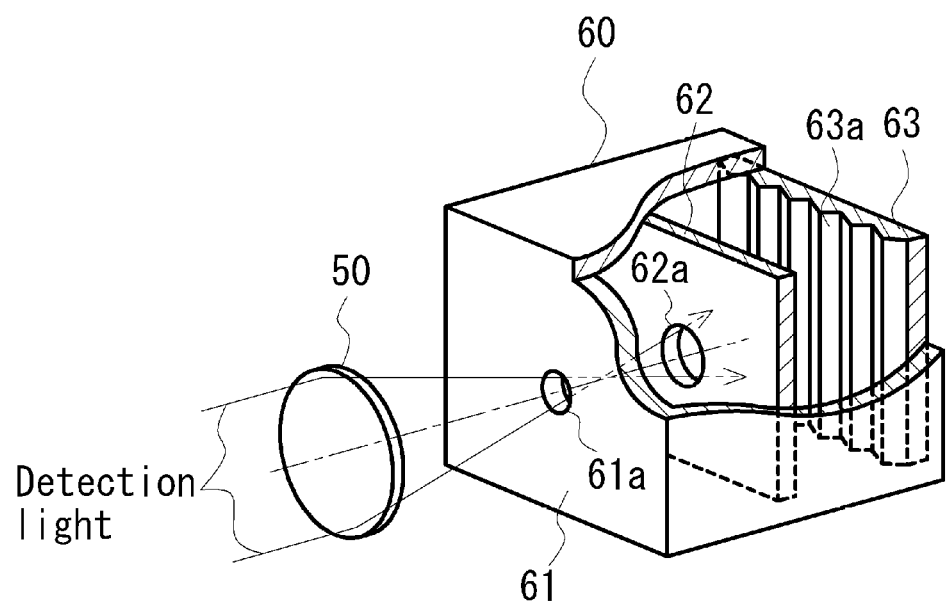
FIG. 3 A perspective view schematically showing the internal configuration of a lens and a light-attenuating structure.

The light-attenuating structure 60 is provided in a predetermined area (in FIG. 2, part of an area in which the light-shielding members 12 are provided) and attenuates incoming light radiated by the lens 50. FIG. 3 is a partially cutaway perspective view schematically showing the internal configuration of the lens 50 and the light-attenuating structure 60. For example, as shown in FIGS. 2 and 3, the light-attenuating structure 60 is formed in a generally rectangular parallelepiped box shape. The light-attenuating structure 60 is placed in a predetermined area such that a plate facing the lens 50 of the plates forming the sides of the light-attenuating structure 60 (referred to as an incident plate 61) is generally orthogonal to the light axis of the lens 50 in proximity to the center of the incident plate 61. Furthermore, a partition plate 62 is provided in parallel to the incident plate 61 in the light-attenuating structure 60. Furthermore, in proximity to the center of the incident plate 61 and the partition plate 62, openings 61a and 62a are provided, centering the light axis of the lens 50. The openings 61a and 62a have a diameter that allows light radiated by the lens 50 to pass through the openings. Also, the openings 61a and 62a are formed such that their diameter increases along the propagation direction of light radiated by the lens 50. Furthermore, an attenuation plate 63 is provided that is irradiated with light radiated by the lens 50 and passing through the opening 61a of the incident plate 61 and the opening 62a of the partition plate 62. The attenuation plate 63 has a face facing the lens 50 (referred to as an irradiated face 63a) that is formed to have a sawtooth cross section. The combination of the light-attenuating structure 60 and the lens 50 provides an internally scattered light suppressing means for suppressing internally scattered light within the light-shielded area.

(Operation)

Next, the operation of the scattered light-type smoke detection apparatus 1 configured as above is described. As shown in FIG. 2, detection light radiated by the light emitter 30 passes through the smoke detection space 20 and enters the lens 50. Detection light entering the lens 50 is collected by the lens 50 and then enters the inside of the light-attenuating structure 60 through the opening 61a provided in the incident plate 61 of the light-attenuating structure 60. Part of the light entering the inside of the light-attenuating structure 60 passes through the opening 62a provided in the partition plate 62 to reach the irradiated face 63a and is reflected by the irradiated face 63a. Another part of the light entering the inside of the light-attenuating structure 60 is reflected by the partition plate 62 and then repeatedly reflected in the area between the incident plate 61 and the partition plate 62 to be gradually attenuated. Here, since the irradiated face 63a is formed to have the sawtooth cross section, most of light reaching the irradiated face 63a is not reflected toward the opening 62a of the partition plate 62, and is reflected toward the inside of the sawtooth groove or toward the wall surface enclosing the space between part other than the opening 62a of the partition plate 62 and the attenuation plate 63, and then is repeatedly reflected in the area between the partition plate 62 and the irradiated face 63a of the attenuation plate 63 to be gradually attenuated. Furthermore, even when part of light reflected in the area between the partition plate 62 and the irradiated face 63a passes through the opening 62a of the partition plate 62, a further fraction of the part of light passes through the opening 61a of the incident plate 61, the further fraction of the part of light being attenuated due to reflection in the area between the partition plate 62 and the irradiated face 63a, so very weak light is radiated from the inside to the outside of the light-attenuating structure 60. Furthermore, light passing through the opening 61a and the opening 62a in the reverse direction is generally confined to a component returning to the light emitter 30. Thus, most of detection light radiated by the light emitter 30 and passing through the smoke detection space 20 is absorbed by the light-attenuating structure 60 and is not internally scattered within the light-shielded area, so internally scattered light entering the light receiver 40 is reduced.

(Effect)

As described above, according to the first embodiment, the internally scattered light suppressing means transmits and guides detection light radiated by the light emitter 30 and passing through the smoke detection space 20 to the predetermined area to suppress internally scattered light within the light-shielded area, which can suppress detection light passing through the smoke detection space 20 and reflected by the base plate 11, the light-shielding members 12, the cover plate or the like to be internally scattered, thereby improving the S/N ratio.

Furthermore, the internally scattered light suppressing means includes: the lens 50 for transmitting and guiding detection light radiated by the light emitter 30 and passing through the smoke detection space 20 to the predetermined area; and the light-attenuating structure 60, provided in the predetermined area, for attenuating incoming light guided by the lens 50, which can cause detection light radiated by the light emitter 30 and passing through the smoke detection space 20 to enter the light-attenuating structure 60 to be attenuated in the light-attenuating structure 60, thereby reliably suppressing detection light passing through the smoke detection space 20 and reflected by the base plate 11, the light-shielding members 12, the cover plate or the like to be internally scattered.

Specifically, the lens 50 collects detection light radiated by the light emitter 30 and passing through the smoke detection space 20 and radiates the collected light to the predetermined area, which can reliably cause detection light radiated by the light emitter 30 and passing through the smoke detection space 20 to enter the light-attenuating structure 60, thereby reliably suppressing detection light passing through the smoke detection space 20 and reflected by the base plate 11, the light-shielding members 12, the cover plate or the like to be internally scattered.

[Second Embodiment]

Next, a second embodiment is described. In the second embodiment, detection light emitted by a light emitter and passing through a smoke detection space is collected by a lens 50 and caused to enter a light-discharging structure provided in a predetermined area, which discharges the entering light to the outside of the light-shielded area. Note that, among components of the second embodiment, components not specifically described are intended to be generally the same as those of the first embodiment. The components generally the same as those of the first embodiment are appropriately denoted by the same numerals and/or names as those used in the first embodiment, and will not be repeatedly described.

(Configuration)

Figure 4:
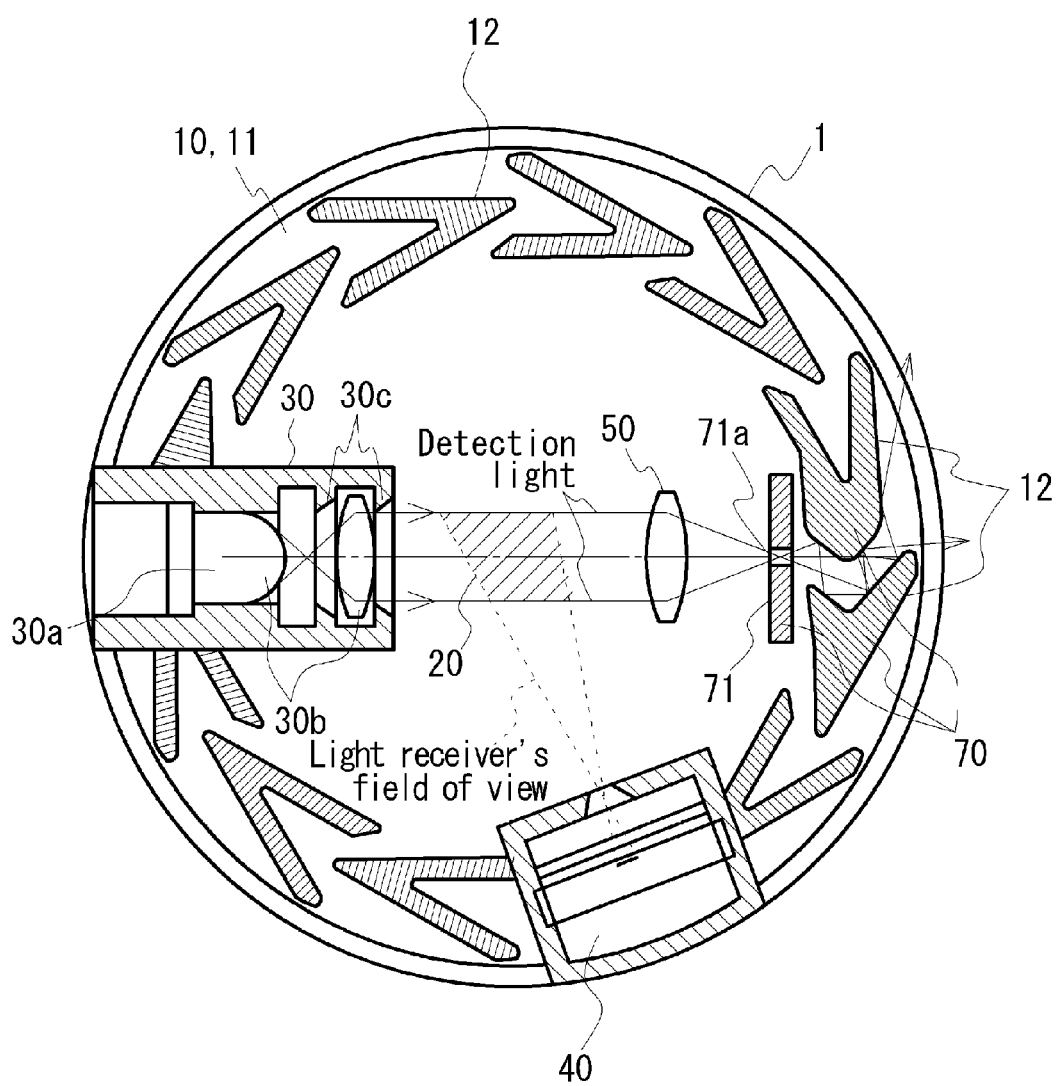
FIG. 4 A cross-sectional view showing a cross section similar to FIG. 2 of a scattered light-type smoke detection apparatus in accordance with a second embodiment.

First, the configuration of a scattered light-type smoke detection apparatus 1 in accordance with the second embodiment is described. FIG. 4 is a cross-sectional view showing a cross section similar to FIG. 2 of the scattered light-type smoke detection apparatus 1 in accordance with the second embodiment. As shown in FIG. 4, the scattered light-type smoke detection apparatus 1 includes a light-discharging structure 70 in place of the light-attenuating structure 60 in the first embodiment.

(Configuration—Light-Discharging Structure)

Figure 5:
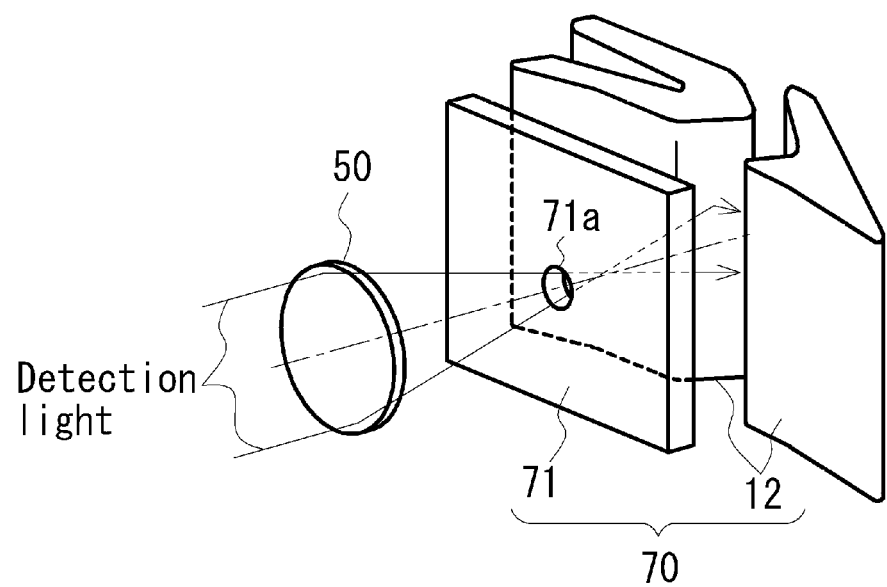
FIG. 5 A perspective view schematically showing the configuration of a lens and a light-discharging structure.

The light-discharging structure 70 is provided in a predetermined area (in FIG. 4, part of an area in which light-shielding members 12 are provided) and discharges incoming light from a lens 50 to the outside of a light-shielded area while light-shielding the light-shielded area from the outside. FIG. 5 is a perspective view schematically showing the configuration of the lens 50 and the light-discharging structure 70. For example, as shown in FIGS. 4 and 5, the light-discharging structure 70 is configured by combining a light-shielding plate 71 with the light-shielding members 12. The light-shielding plate 71 is placed between the lens 50 and the light-shielding members 12 such that the plate surface is generally orthogonal to the light axis of the lens 50. In proximity to the center of the light-shielding plate 71, an opening 71a is provided, centering the light axis of the lens 50. The opening 71a has a diameter that allows light from the lens 50 to pass through the opening 71a. Furthermore, the light-shielding members 12 are placed such that light passing through the lens 50 and the opening 71a enters between light-shielding members 12 adjacent to each other of the light-shielding members 12. The combination of the light-discharging structure 70 and the lens 50 provides an internally scattered light suppressing means for suppressing internally scattered light within the light-shielded area. Two of the light-shielding members 12 positioned behind the light-shielding plate 71 in FIG. 4 are formed and placed so as to reflect most of light passing through the opening 71a toward the outside of the light-shielded area. Here, even when a component that is reflected by the two light-shielding members 12 toward the inside of the light-shielded area exists, most of the component is blocked by the light-shielding plate 71, and only a fraction of the component passes through the opening 71a in the reverse direction, and furthermore, the component passing through the opening 71a is further limited due to thickness of the opening 71a (light-shielding plate 71), so the component propagating in the reverse direction returns to the light emitter 30 through the lens 50. Accordingly, the component propagating in the reverse direction rarely enters the light receiver 40 after being further reflected by another light-shielding member 12 or the like.

(Operation)

Next, the operation of the scattered light-type smoke detection apparatus 1 configured as above is described. As shown in FIG. 4, detection light radiated by the light emitter 30 passes through the smoke detection space 20 and enters the lens 50. Detection light entering the lens 50 is collected by the lens 50 and then enters a space between the light-shielding members 12 adjacent to each other through the opening 71a provided in the light-shielding plate 71 of the light-discharging structure 70. Light entering the space between the light-shielding members 12 adjacent to each other is repeatedly reflected between the surfaces of the light-shielding members 12 to be gradually attenuated, part of which is discharged to the outside of the light-shielded area. Furthermore, even when part of light entering the space between the light-shielding members 12 adjacent to each other is reflected by the light-shielding members 12 toward the inside of the light-shielded area, a further fraction of the part of light passes through the opening 71a of the light-shielding plate 71, the further fraction of the part of light being attenuated due to reflection by the surfaces of the light-shielding members 12, so very weak light passes through the opening 71a of the light-shielding plate 71 and enters the inside of the light-shielded area again. Thus, most of detection light radiated by the light emitter 30 and passing through the smoke detection space 20 is discharged to the outside of the light-shielded area by the light-discharging structure 70 or absorbed by the light-discharging structure 70, and is not internally scattered within the light-shielded area, so internally scattered light entering the light receiver 40 is reduced. Furthermore, the light-shielded area is light-shielded from the outside by the light-shielding members 12.

(Effect)

As described above, according to the second embodiment, the internally scattered light suppressing means transmits and guides detection light radiated by the light emitter 30 and passing through the smoke detection space 20 through the lens 50 to the outside of the light-shielded area to suppress internally scattered light within the light-shielded area, which can suppress detection light passing through the smoke detection space 20 and reflected by the base plate 11, another light-shielding member 12, the cover plate or the like to be internally scattered, thereby improving the S/N ratio.

Furthermore, the internally scattered light suppressing means includes: the lens 50 for transmitting and guiding detection light radiated by the light emitter 30 and passing through the smoke detection space 20 to the predetermined area; and the light-discharging structure 70, provided in the predetermined area, for discharging incoming light guided by the lens 50 to the outside of the light-shielded area while light-shielding the light-shielded area from the outside, which can cause detection light radiated by the light emitter 30 and passing through the smoke detection space 20 to enter the light-discharging structure 70 to be discharged through the light-discharging structure 70 to the outside of the light-shielded area, thereby reliably suppressing detection light passing through the smoke detection space 20 and reflected by the base plate 11, another light-shielding member 12, the cover plate or the like to be internally scattered.

Furthermore, the lens 50 collects detection light radiated by the light emitter 30 and passing through the smoke detection space 20 and radiates the collected light to the predetermined area, which can reliably cause detection light radiated by the light emitter 30 and passing through the smoke detection space 20 to enter the light-discharging structure 70, thereby reliably suppressing detection light passing through the smoke detection space 20 and reflected by the base plate 11, another light-shielding member 12, the cover plate or the like to be internally scattered.

[Third Embodiment]

Finally, a third embodiment is described. The third embodiment includes a prism, in which detection light emitted by a light emitter and passing through a smoke detection space enters the prism through one end face, then the light entering the prism is guided from the one end face to the other end face, and then the guided light is radiated from the other end face to a predetermined area in a light-shielded area. Note that, among components of the third embodiment, components not specifically described are intended to be generally the same as those of the first embodiment. The components generally the same as those of the first embodiment are appropriately denoted by the same numerals and/or names as those used in the first embodiment, and will not be repeatedly described.

(Configuration)

Figure 6:
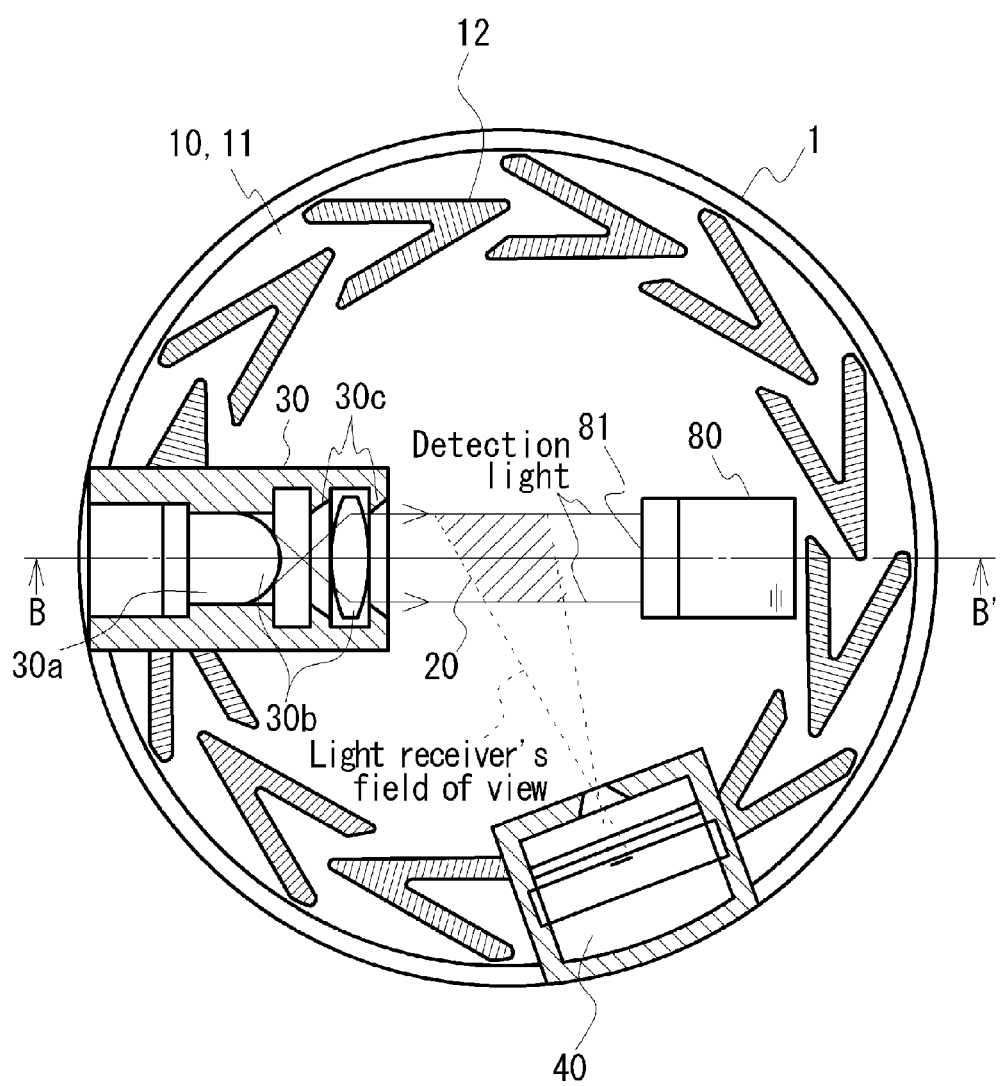
FIG. 6 A cross-sectional view showing a cross section similar to FIG. 2 of a scattered light-type smoke detection apparatus in accordance with a third embodiment.

First, the configuration of a scattered light-type smoke detection apparatus 1 in accordance with the third embodiment is described. FIG. 6 is a cross-sectional view showing a cross section similar to FIG. 2 of the scattered light-type smoke detection apparatus 1 in accordance with the third embodiment. As shown in FIG. 6, the scattered light-type smoke detection apparatus 1 includes a prism 80 in place of the lens 50 in the first embodiment.

(Configuration—Prism)

Figure 7:
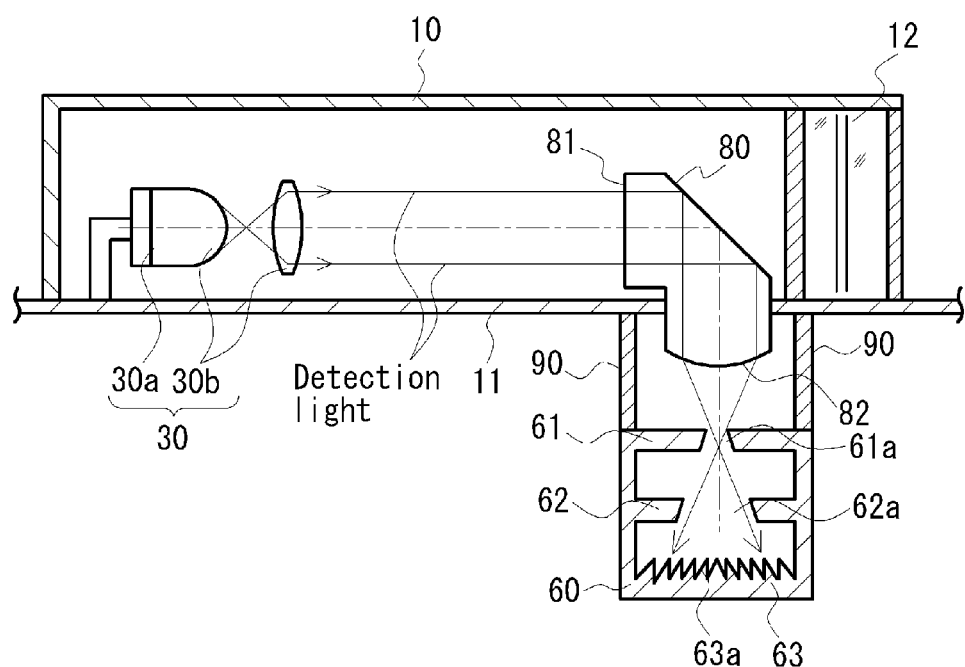
FIG. 7 A longitudinal cross-sectional view showing a cross section taken along the line B-B' of the scattered light-type smoke detection apparatus shown in FIG. 6.

In the prism 80, detection light radiated by a light emitter 30 and passing through a smoke detection space 20 enters the prism 80 through one end face, then the light entering the prism 80 is transmitted and guided from the one end face to the other end face, and then the guided light is radiated from the other end face to a predetermined area. This causes detection light radiated by the light emitter 30 and passing through the smoke detection space 20 to be guided to the predetermined area. FIG. 7 is a longitudinal cross-sectional view showing a cross section taken along the line B-B' of the scattered light-type smoke detection apparatus 1 shown in FIG. 6. As shown in FIG. 7, the prism 80 is formed to have an L-shaped side cross section and is placed so as to penetrate a base plate 11. One end face of the prism 80 (referred to as an incident face 81) is placed so as to face the light emitter 30 with the smoke detection space 20 in between and is formed so as to be generally orthogonal to the light axis of the light emitter 30 in proximity to the center of the incident face 81. On the other hand, the other end face through which light entering the prism 80 through the incident face 81 and guided through the prism 80 is radiated (referred to as a radiation face 82) is formed so as to be generally parallel to the base plate 11 outside a main body 10 (in FIG. 7, below the base plate 11). Furthermore, the radiation face 82 is formed as a lens face for collecting light guided through the prism 80 and radiating the collected light to a light-attenuating structure 60.

(Configuration—Light-Attenuating Structure)

As shown in FIG. 7, the light-attenuating structure 60 is placed outside the main body 10 such that the plate surface of an incident plate 61 of the light-attenuating structure 60 is generally orthogonal to the light axis of the radiation face 82 of the prism 80 in proximity to the center of the incident plate 61. Furthermore, in the light-attenuating structure 60, a partition plate 62 is provided that is generally orthogonal to the light axis of the radiation face 82 of the prism 80. Furthermore, in proximity to the center of the incident plate 61 and the partition plate 62, openings 61a and 62a are provided, centering the light axis of the radiation face 82 of the prism 80, respectively. The openings 61a and 62a have a diameter that allows light radiated from the radiation face 82 of the prism 80 to pass through the openings. Furthermore, an attenuation plate 63 is provided that is irradiated with light radiated by the radiation face 82 of the prism 80 and passing through the opening 61a of the incident plate 61 and the opening 62a of the partition plate 62, the attenuation plate 63 having an irradiated face 63a that is formed to have a sawtooth cross section. The combination of the light-attenuating structure 60 and the prism 80 provides an internally scattered light suppressing means for suppressing internally scattered light within the light-shielded area.

Furthermore, as shown in FIG. 7, the area between the light-attenuating structure 60 and the base plate 11 is enclosed by a light-shielding wall 90 to light-shielding the prism 80 from the outside of the main body 10, which prevents light from the outside of the main body 10 from entering the prism 80 and then entering the light-shielded area through the prism 80.

(Configuration—Operation)

Next, the operation of the scattered light-type smoke detection apparatus 1 configured as above is described. As shown in FIG. 7, detection light radiated by the light emitter 30 passes through the smoke detection space 20 and enters the prism 80 through the incident face 81. Detection light entering the prism 80 through the incident face 81 is guided from the incident face 81 through the prism 80 to the radiation face 82, then is collected by a lens formed on the radiation face 82, and then enters the inside of the light-attenuating structure 60 through the opening 61a provided in the incident plate 61 of the light-attenuating structure 60. Light entering the inside of the light-attenuating structure 60 passes through the opening 62a provided in the partition plate 62 to reach the irradiated face 63a and is reflected by the irradiated face 63a. Here, since the irradiated face 63a is formed to have the sawtooth cross section, most of light reaching the irradiated face 63a is not reflected toward the opening 62a of the partition plate 62, and is reflected toward the inside of the sawtooth groove or toward the wall surface enclosing the space between part other than the opening 62a of the partition plate 62 and the attenuation plate 63, and then is repeatedly reflected in the area between the partition plate 62 and the irradiated face 63a of the attenuation plate 63 to be gradually attenuated. Furthermore, even when part of light reflected in the area between the partition plate 62 and the irradiated face 63a passes through the opening 62a of the partition plate 62, a further fraction of the part of light passes through the opening 61a of the incident plate 61, the further fraction of the part of light being attenuated due to reflection in the area between the partition plate 62 and the irradiated face 63a, so very weak light is radiated from the opening 61a of the incident plate 61 to the outside of the light-attenuating structure 60. Furthermore, light passing through the opening 61a and the opening 62a in the reverse direction is generally confined to a component returning to the light emitter 30 through the prism 80. Thus, most of detection light radiated by the light emitter 30 and passing through the smoke detection space 20 is absorbed by the light-attenuating structure 60 and is not internally scattered within the light-shielded area, so internally scattered light entering the light receiver 40 is reduced.

(Effect)

As described above, according to the third embodiment, detection light radiated by the light emitter 30 and passing through the smoke detection space 20 enters the prism 80 through the incident face 81, then the entering light is guided from the incident face 81 to the radiation face 82, and then the guided light is radiated from the radiation face 82 to the predetermined area, which can reliably cause detection light radiated by the light emitter 30 and passing through the smoke detection space 20 to enter the light-attenuating structure 60, thereby reliably suppressing detection light passing through the smoke detection space 20 and reflected by the base plate 11, the light-shielding members 12, the cover plate or the like to be internally scattered.

Specifically, the radiation face 82 of the prism 80 is formed as the lens face for collecting light guided through the prism 80 and radiating the collected light to the predetermined area, which can more reliably cause light radiated from the radiation face 82 of the prism 80 to enter the light-attenuating structure 60, thereby reliably suppressing detection light passing through the smoke detection space 20 and reflected by the base plate 11, the light-shielding members 12, the cover plate or the like to be internally scattered.

[III] Variation of Embodiments

While the embodiments in accordance with the invention have been described above, the specific configurations and means of the invention may be varied and modified in any appropriate way without departing from the scope of the technical spirit of the invention described in the claims. Now, such a variation is described.

(About Problems to be Solved and Advantage of the Invention)

First, the problem to be solved and the advantage of the invention are not limited to what has been described above, but the invention may solve a problem not described above or may achieve an effect not described above, or the invention may solve only part of the problem described above or may achieve only part of the effect described above.

(About Lens)

Figure 8:
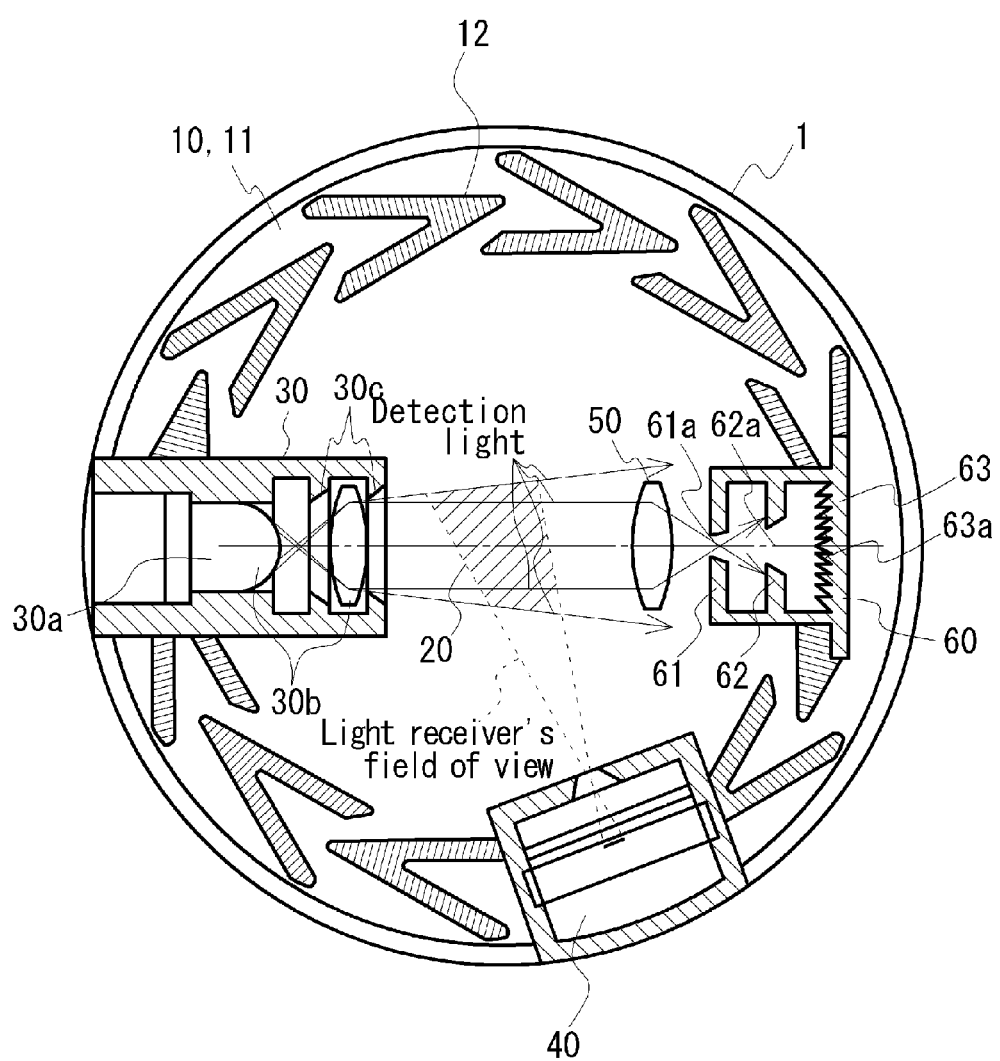
FIG. 8 A cross-sectional view showing a cross section taken along the line A-A' of the scattered light-type smoke detection apparatus shown in FIG. 1(b).

In the first and second embodiments described above, the case in which the whole of detection light radiated by the light emitter 30 and passing through the smoke detection space 20 enters the lens 50 has been described as an example, however, as shown in FIG. 8, the lens 50 may be configured to collect part of detection light radiated by the light emitter 30 and passing through the smoke detection space 20, the collected light being radiated to the predetermined area (in FIG. 8, the area in which the light-attenuating structure 60 is provided). Specifically, for example, the lens 50 may have an outer diameter that is smaller than the outer diameter of light flux of detection light at the incident position to the lens 50 so that part of detection light does not enter the lens 50. In this case, the part of detection light not entering the lens 50 is reflected by the base plate 11, the light-shielding members 12 or the cover plate to be internally scattered. In this way, part of detection light passing through the smoke detection space 20 may be intentionally caused to be internally scattered, thereby adjusting the zero point level of the detection output of the light receiver 40 to a predetermined value. If the zero point level is too high, a problem may occur in which the S/N ratio decreases. If the zero point level is too low, a problem may occur in which it is difficult to distinguish scattered light from a failure of the light emitter 30 or the light receiver 40 (failure in light emitting or light receiving). If the zero point level is unstable, a problem may occur in which the operation is also unstable. However, adjusting the zero point level to a predetermined level as above can facilitate implementation of operation confirmation or the like of the light emitter 30 and the light receiver 40 while suppressing decrease in the S/N ratio, thereby stabilizing the operation. Similarly, when using the prism 80 as in the third embodiment, the prism 80 may be configured so that part of detection light passing through the smoke detection space 20 enters the prism 80 through the incident face 81. Note that the zero point level may also be adjusted to a predetermined value by forming the opening 61a of the incident plate 61 and the opening 62a of the partition plate 62 with an appropriate diameter and intentionally causing light to travel in the reverse direction from the light-attenuating structure 60 to the light-shielded area.

(About Prism)

Figure 9:
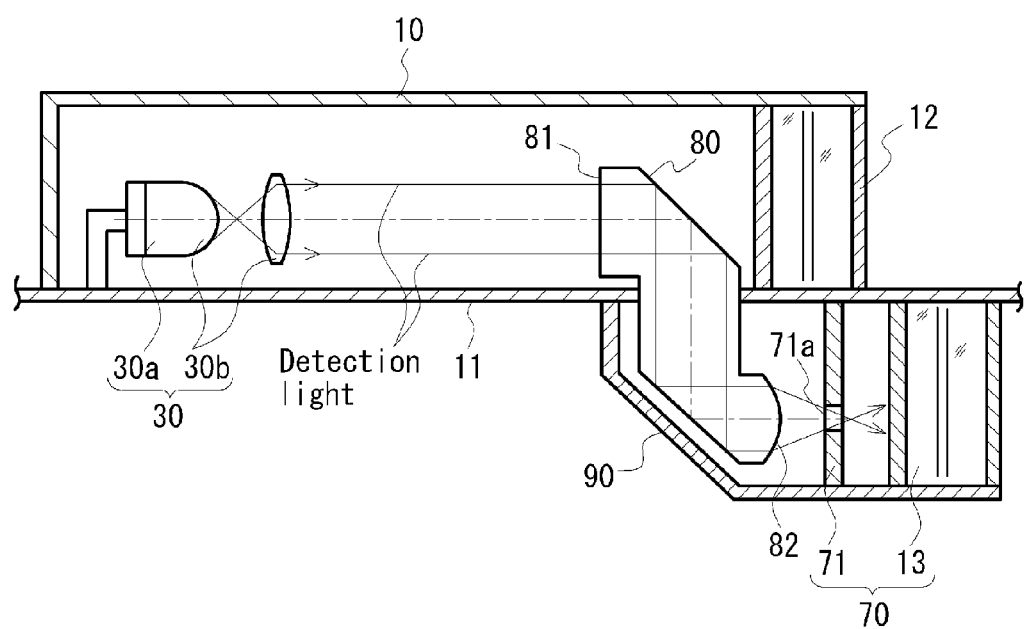
FIG. 9 A longitudinal cross-sectional view schematically showing a case in which a light-discharging structure is provided in place of the light-attenuating structure in the scattered light-type smoke detection apparatus in accordance with the third embodiment.

In the third embodiment described above, light radiated from the prism 80 through the radiation face 82 is configured to enter the light-attenuating structure 60. However, light radiated from the prism 80 through the radiation face 82 may also be configured to enter a light-discharging structure 70. FIG. 9 is a longitudinal cross-sectional view schematically showing a case in which the light-discharging structure 70 is provided in place of the light-attenuating structure 60 in the scattered light-type smoke detection apparatus 1 in accordance with the third embodiment. In the example shown in FIG. 9, a right angle prism is added to the prism 80 illustrated in the third embodiment so that light is radiated in a direction parallel to the base plate 11. A light-shielding plate 71 of the light-discharging structure 70 is provided so as to face a radiation face 82 of the right angle prism. In the light-shielding plate 71, an opening 71a is provided, centering the light axis of the radiation face 82 of the prism 80. The opening 71a has a diameter that allows light radiated from the prism 80 to pass through the opening 71a. Furthermore, light-shielding members 13 are provided between the outside of the scattered light-type smoke detection apparatus 1 and the light-shielding plate 71.

In this case, as shown in FIG. 9, detection light radiated by the light emitter 30 passes through the smoke detection space 20 and enters the prism 80 through the incident face 81. Detection light entering the prism 80 through the incident face 81 is guided through the prism 80 from the incident face 81 to the radiation face 82, then is radiated from the radiation face 82, and then enters a space between the light-shielding members 13 adjacent to each other through the opening 71a provided in the light-shielding plate 71 of the light-discharging structure 70. Light entering the space between the light-shielding members 13 adjacent to each other is repeatedly reflected between the surfaces of the light-shielding members 13 to be gradually attenuated, part of which is discharged to the outside of the light-shielded area. Furthermore, even when part of light entering the space between the light-shielding members 13 adjacent to each other is reflected by the light-shielding members 13 toward the inside of the light-shielded area, a further fraction of the part of light passes through the opening 71a of the light-shielding plate 71, the further fraction of the part of light being attenuated due to reflection by the surfaces of the light-shielding members 13, so very weak light passes through the opening 71a of the light-shielding plate 71 and enters the inside of the light-shielded area again through the prism 80. Thus, most of detection light radiated by the light emitter 30 and passing through the smoke detection space 20 is discharged to the outside of the light-shielded area by the light-discharging structure 70 or absorbed by the light-discharging structure 70, and is not internally scattered within the light-shielded area, so internally scattered light entering the light receiver 40 is reduced. Furthermore, the light-shielded area is light-shielded from the outside by the light-shielding members 13. Note that the placement and shape of the light-shielding members 13 may be different from those of the light-shielding members 12.

One embodiment of the present invention provides a scattered light-type smoke detection apparatus according to claim 1 includes: a smoke detection space that is provided in a light-shielded area that is light-shielded from the outside, into which smoke particles flow from the outside; a light emitter for emitting detection light toward the smoke detection space; and a light receiver for receiving scattered light caused by detection light emitted by the light emitter and scattered by smoke particles flowing into the smoke detection space, wherein the scattered light-type smoke detection apparatus includes an internally scattered light suppressing means for transmitting and guiding part or the whole of detection light emitted by the light emitter and passing through the smoke detection space to a predetermined area or the outside of the light-shielded area to suppress internally scattered light within the light-shielded area.

Another embodiment of the present invention provides the scattered light-type smoke detection apparatus according to the above embodiment, wherein the internally scattered light suppressing means includes: a light-guiding means for transmitting and guiding part or the whole of detection light emitted by the light emitter and passing through the smoke detection space to the predetermined area; and a light-attenuating structure, provided in the predetermined area, for attenuating incoming light guided by the light-guiding means.

Another embodiment of the present invention provides the scattered light-type smoke detection apparatus according to the above embodiment, the internally scattered light suppressing means includes: a light-guiding means for transmitting and guiding part or the whole of detection light emitted by the light emitter and passing through the smoke detection space to the predetermined area; and a light-discharging structure, provided in the predetermined area, for discharging incoming light guided by the light-guiding means to the outside of the light-shielded area while light-shielding the light-shielded area from the outside.

Another embodiment of the present invention provides the scattered light-type smoke detection apparatus according to the above embodiment, the light-guiding means is a lens that collects part or the whole of detection light emitted by the light emitter and passing through the smoke detection space and radiates the collected light to the predetermined area.

Another embodiment of the present invention provides the scattered light-type smoke detection apparatus according to the above embodiment, the light-guiding means is a prism in which part or the whole of detection light emitted by the light emitter and passing through the smoke detection space enters the prism through one end face, then the light entering the prism is guided from the one end face to the other end face, and then the guided light is radiated from the other end face to the predetermined area.

Another embodiment of the present invention provides the scattered light-type smoke detection apparatus according to the above embodiment, the other end face of the prism is formed as a lens face for collecting light guided through the prism and radiating the collected light to the predetermined area.

According to the above embodiments of the present invention, the following technical effects can be obtained.

The internally scattered light suppressing means transmits and guides part or the whole of detection light emitted by the light emitter and passing through the smoke detection space to the predetermined area or the outside of the light-shielded area to suppress internally scattered light within the light-shielded area, which can further suppress internally scattered light caused by detection light passing through the smoke detection space and reflected by the light-shielding member, than before, and can improve the S/N ratio by appropriately adjusting internally scattered light.

Further, the internally scattered light suppressing means includes: the light-guiding means for transmitting and guiding part or the whole of detection light emitted by the light emitter and passing through the smoke detection space to the predetermined area; and the light-attenuating structure, provided in the predetermined area, for attenuating incoming light guided by the light-guiding means, which can cause detection light emitted by the light emitter and passing through the smoke detection space to enter the light-attenuating structure to be attenuated in the light-attenuating structure, thereby reliably suppressing detection light passing through the smoke detection space and reflected by the light-shielding members to be internally scattered.

Furthermore, the internally scattered light suppressing means includes: the light-guiding means for transmitting and guiding part or the whole of detection light emitted by the light emitter and passing through the smoke detection space to the predetermined area; and the light-discharging structure, provided in the predetermined area, for discharging incoming light guided by the light-guiding means to the outside of the light-shielded area while light-shielding the light-shielded area from the outside, which can cause detection light emitted by the light emitter and passing through the smoke detection space to enter the light-discharging structure to be discharged through the light-discharging structure to the outside of the light-shielded area, thereby reliably suppressing detection light passing through the smoke detection space and reflected by the light-shielding members to be internally scattered.

Furthermore, the lens collects part or the whole of detection light emitted by the light emitter and passing through the smoke detection space and radiates the collected light to the predetermined area, which can reliably cause detection light emitted by the light emitter and passing through the smoke detection space to enter the light-attenuating structure or the light-discharging structure, thereby reliably suppressing detection light passing through the smoke detection space and reflected by the light-shielding members to be internally scattered.

Furthermore, part or the whole of detection light emitted by the light emitter and passing through the smoke detection space enters the prism through the incident face, then the entering light is guided from the incident face to the radiation face, and then the guided light is radiated from the radiation face to the predetermined area, which can reliably cause detection light emitted by the light emitter and passing through the smoke detection space to enter the light-attenuating structure or the light-discharging structure, thereby reliably suppressing detection light passing through the smoke detection space and reflected by the light-shielding members to be internally scattered.

Furthermore, the radiation face of the prism is formed as the lens face for collecting light guided through the prism and radiating the collected light to the predetermined area, which can more reliably cause light radiated from the radiation face of the prism to enter the light-attenuating structure or the light-discharging structure, thereby reliably suppressing detection light passing through the smoke detection space and reflected by the light-shielding members to be internally scattered.

DESCRIPTION OF REFERENCE NUMERALS AND SIGNS 1 scattered light-type smoke detection apparatus
2 smoke sensor
3 chassis
10 main body
11 base plate
12, 13 light-shielding members
20 smoke detection space
30 light emitter
30a LED
30b, 50 lens
30c aperture
40 light receiver
60 light-attenuating structure
61 incident plate
62 partition plate
61a, 62a, 71a opening
63 attenuation plate
63a irradiated face
70 light-discharging structure
71 light-shielding plate
80 prism
81 incident face
82 radiation face
90 light-shielding wall

The invention claimed is:

1. A scattered light-type smoke detection apparatus comprising:
 a smoke detection space that is provided in a light-shielded area that is light-shielded from the outside, into which smoke particles flow from the outside;
 a light emitter for emitting detection light toward the smoke detection space; and
 a light receiver for receiving scattered light caused by detection light emitted by the light emitter and scattered by smoke particles flowing into the smoke detection space,
 wherein the scattered light-type smoke detection apparatus comprises, a lens that suppresses internally scattered light within the light-shielded area by collecting part or the whole of detection light emitted by the light emitter and passing through the smoke detection space and radiating the collected light to the predetermined area, and a light-attenuating structure, provided in the predetermined area, for attenuating incoming light guided by the lens, or a light-discharging structure, provided in the predetermined area, for discharging incoming light guided by the lens to the outside of the light-shielded area while light-shielding the light-shielded area from the outside, wherein the lens is arranged between the smoke detection space and the light-attenuating structure or the light-discharging structure.

2. The scattered light-type smoke detection apparatus according to claim 1, wherein the scattered light-type smoke detection apparatus comprises the light-attenuating structure, the light-attenuating structure has a plate facing the lens and defining an opening to which light radiated by the lends is passed, and a diameter of the opening is smaller than a diameter of the lends.

3. The scattered light-type smoke detection apparatus according to claim 1, wherein, the scattered light-type smoke detection apparatus comprises the light-discharging structure, the light-discharging structure has a plate facing the lens and defining an opening to which light radiated by the lends is passed, and a diameter of the opening is smaller than a diameter of the lends.

* * * * *